United States Patent
Seligman

(10) Patent No.: US 7,627,378 B2
(45) Date of Patent: Dec. 1, 2009

(54) BATTERY MONITOR AND POWER DEMAND ADJUSTER

(75) Inventor: Peter Seligman, Lane Cove (AU)

(73) Assignee: Cochlear Limited, Lane Cove (AU)

( * ) Notice: Subject to any disclaimer, the term of this patent is extended or adjusted under 35 U.S.C. 154(b) by 229 days.

(21) Appl. No.: 11/543,815

(22) Filed: Oct. 6, 2006

(65) Prior Publication Data
US 2007/0032838 A1  Feb. 8, 2007

Related U.S. Application Data

(63) Continuation of application No. 10/257,170, filed as application No. PCT/AU00/00305 on Apr. 11, 2000, now Pat. No. 7,120,500.

(51) Int. Cl.
*A61N 1/36* (2006.01)
(52) U.S. Cl. ...................................................... 607/56
(58) Field of Classification Search .................. 600/17, 600/16
See application file for complete search history.

(56) References Cited

U.S. PATENT DOCUMENTS

| | | | |
|---|---|---|---|
| 4,120,307 A | 10/1978 | Jirak et al. | |
| 4,590,941 A | 5/1986 | Saulson et al. | |
| 5,193,538 A * | 3/1993 | Ekwall | 607/29 |
| 5,457,365 A | 10/1995 | Blagalia et al. | |
| 5,562,595 A * | 10/1996 | Neisz | 600/16 |
| 5,668,465 A | 9/1997 | May | |
| 5,773,961 A | 6/1998 | Cameron et al. | |
| 5,869,970 A | 2/1999 | Palm et al. | |
| 5,870,685 A | 2/1999 | Flynn | |
| 5,963,255 A | 10/1999 | Anderson et al. | |
| 6,219,580 B1 * | 4/2001 | Faltys et al. | 607/57 |
| 6,430,441 B1 * | 8/2002 | Levine | 607/28 |
| 7,006,865 B1 * | 2/2006 | Cohen et al. | 607/5 |

FOREIGN PATENT DOCUMENTS

| | | |
|---|---|---|
| EP | 0 653 826 | 5/1995 |
| JP | 06-178456 | 6/1994 |
| JP | 10-108387 A | 9/1996 |
| JP | 10-108385 | 4/1998 |
| WO | WO 97/01314 | 1/1997 |

OTHER PUBLICATIONS

International Search Report, dated Jun. 26, 2000 for International Patent Application No. PCT/AU2000/000305.
Written Opinion, dated Nov. 29, 2001 for International Patent Application No. PCT/AU2000/000305.
International Preliminary Examination Report, dated Feb. 8, 2002, for International Patent Application No. PCT/AU2000/000305.
Supplementary European Search Report, dated Jan. 20, 2005 for EP 00 91 5037.

* cited by examiner

*Primary Examiner*—Carl H. Layno
*Assistant Examiner*—Jon-Eric C. Morales
(74) *Attorney, Agent, or Firm*—Connolly Bove Lodge & Hutz LLP

(57) ABSTRACT

A system for monitoring and controlling power demands in devices with DC power supplies is disclosed. In response to a detected decline in voltage levels, the device reduces the power demands of the device, in one or more stages, before powering down entirely. This approach has application to battery powered devices, particularly for medical applications such as cochlear implants.

30 Claims, 3 Drawing Sheets

BATTERY MONITOR AND POWER DEMAND ADJUSTER

CROSS-REFERENCE TO RELATED APPLICATIONS

This application is a continuation of U.S. patent application Ser. No. 10/257,170 filed on Dec. 22, 2002 now U.S. Pat. No. 7,120,500, "Battery Monitor and Power Demand Adjuster" which is a national stage application of PCT/AU2000/000305 entitled, "Battery Monitor and Power Demand Adjuster" and filed on Apr. 11, 2000.

TECHNICAL FIELD

The present invention relates generally to devices powered by energy storage arrangements, and in particular but not exclusively to prostheses and stimulation devices powered by batteries.

BACKGROUND ART

Many devices are powered by electrochemical cells, particularly devices for medical use. Examples of such devices include hearing prostheses, neural stimulators, pacers, drug pumps and other devices. Increasingly, these devices use digital processing systems, rather than analog systems which were the standard prior art technique. One feature of digital systems is that the processor used will generally require a certain minimum voltage to operate effectively. If this is not present, the device will fail erratically. To avoid this, a system shutdown voltage level is generally used, at which level the device shuts itself down. This level is often set well above the actual minimum level, to avoid the possibility of error from a dubious power supply. In contrast, prior art analog systems generally fail gradually, with progressively less performance delivered as less voltage is available from the battery. Accordingly, the user has generally more warning of impending device failure.

To take the example of cochlear implants, modern speech processors are controlled by and process speech using a microprocessor. The speech processor also provides power to an induction loop, which via an inductive coupling supplies power and data to an implanted receiver stimulator unit. Although in principle any suitable battery could be used to provide power to such systems, the zinc-air cell is the preferred power source. Such cells are also commonly used for applications such as external hearing aids.

Zinc air cells have several practical advantages. They have a very high energy density, and so can supply a device's requirements for a relatively long period of time relative to their size and weight. They also have a relatively constant power output through most of their life, so that there is little risk of dangerous rapid discharge, for example by shorting. However, if they experience a heavy load, then it is common for the voltage to temporarily sag.

Conventionally, such devices have employed a battery monitor arrangement, whereby the voltage is monitored and if it falls below a certain level, the device is shut down. Such voltage levels are often set at a value which corresponds to a relatively high power demand, so as to prevent anomalous operation due to under voltage. As a result, if even a relatively new battery is subjected to adverse conditions, for example a period of heavy load, the cell voltage may fall below the pre-defined cut-off level and the processor will be shut down. In the field of Cochlear implants such an event is inconvenient and has potentially serious implications. After shut-down, the user must reset the speech processor by re-starting it, and hence the user is disconnected for a time from their hearing environment. Similar problems can arise with other battery powered digital systems, where short term conditions cause a temporary reduction in the voltage of the power supply.

It is an object of the present invention to provide an improved battery monitoring arrangement in order to improve the performance of battery powered devices.

SUMMARY OF THE INVENTION

The present invention provides, broadly, for a device in which battery performance is monitored, and in which the power demands of a device are reduced to match the available battery power. This allows for what may be called graceful failure, rather than complete shut-down at an arbitrary level.

In the case of a cochlear implant, one implementation is to introduce a series of battery voltage trigger levels, at or below which levels aspects of processor performance are downgraded. A preferred implementation progressively reduces the stimulation rate as the battery voltage declines, until it ultimately reaches a shut-down level. However, if the battery voltage increases before shut-down level is achieved, the stimulation rate is progressively increased to normal levels. This allows the device to cope with a degree of voltage sag without ceasing to function.

Alternative responses to a reduction in voltage for a cochlear implant implementation may include a change in the speech processing strategy, or other changes to reduce power requirements. In other devices, the performance of the device may be reduced by changes in the operation of processors or other elements, without shutting down the system. These alternatives may be used separately or in combination.

Whilst the present invention has particular advantages for zinc-air cells, the principle has application to other battery-powered digital devices, especially devices whose continued function, even at a reduced level of performance, is important.

BRIEF DESCRIPTION OF DRAWINGS

An implementation of the present invention will now be described with reference to the accompanying figures, in which.

DESCRIPTION

The present invention will be described with particular reference to a speech processor unit for a cochlear implant system. However, it will be appreciated that the present invention has application to other devices using a battery to power a digital device, with modifications appropriate to the application as would be apparent to those skilled in the art. The implementation is intended to illustrate the invention's application to a particular situation, being a speech processor for an intracochlear implant.

Figure 1:
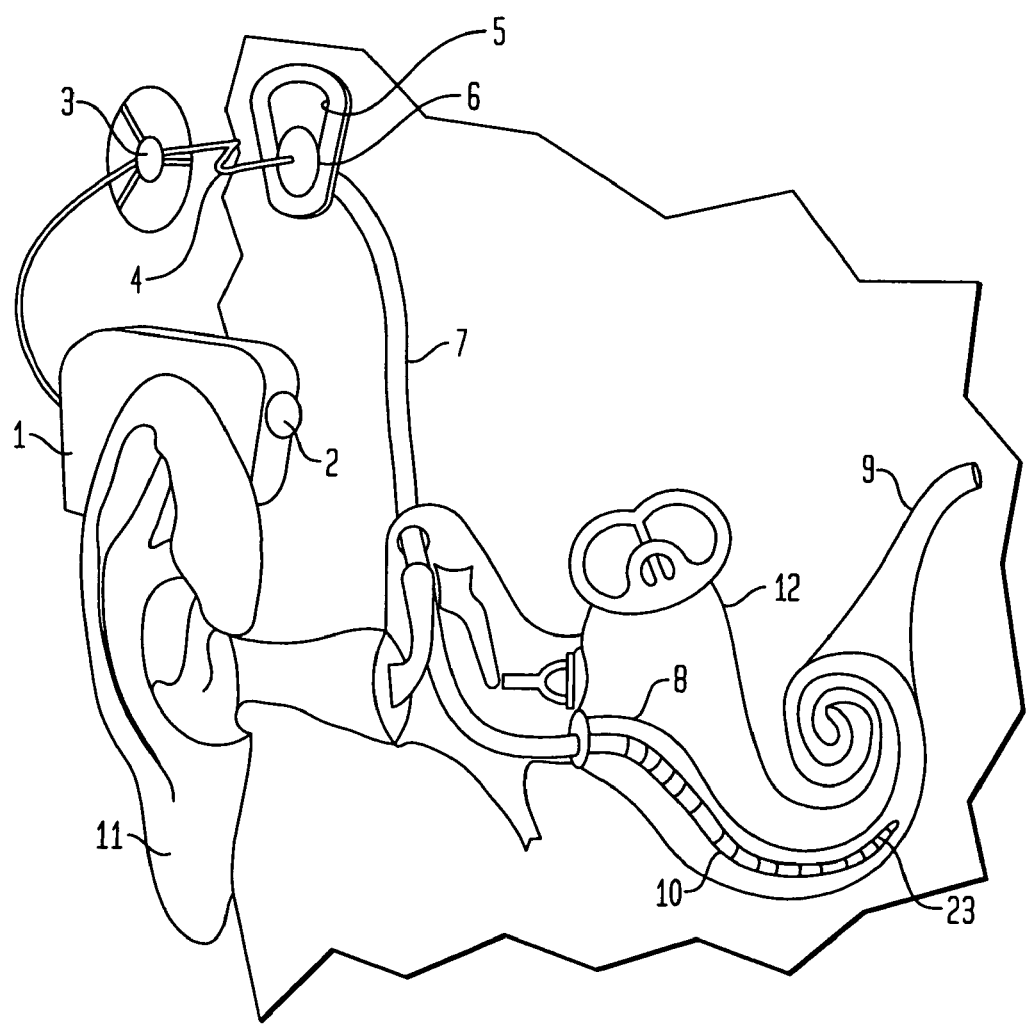
FIG. 1 is a schematic illustration of a conventional intra-cochlear implant system.

Referring to FIG. 1, a typical cochlear implant device is shown. It will be appreciated that such an arrangement is well known in the art, and that the illustration and the following discussion are intended purely to provide a context for the present invention. From this figure can be seen the external component, including a speech processor 1, and an internal component including an implanted receiver and stimulator unit 6. The external component further includes a microphone 2 which is shown integral with the speech processor 1. The speech processor is in this illustration constructed and arranged so that it can fit behind the outer ear 11. Alternative versions may be worn on the body. Attached to speech processor 1 is a transmitter coil 3 which transmits the electrical signals to the implanted unit 6 via an RF link 4.

The implanted component includes a receiver coil 5 for receiving power and data from coil 3. A cable 7 extends from the implanted device 6 to the cochlea 12 and terminates in an electrode array 10. The signals thus received are applied by the array 10 to the basilar membrane 8 thereby stimulating the auditory nerve 9. The operation of the device shown in FIG. 1 is described, for example, in the applicant's U.S. Pat. No. 4,532,930, the disclosure of which is hereby incorporated by reference.

Thus, the RF link, which is in turn powered by the speech processor 1, provides power and data to the implanted device 6. The speech processor also processes sound signals received by microphone 2, so as to send appropriate instructions for stimulation to the implanted device 6. The precise details of speech processing are not necessary for an understanding of the present invention, and the skilled worker in the art will be aware that many such schemes have been used and proposed. What is pertinent is that some of these schemes, and their modes of operation, consume variable levels of power. For example, a higher rate of stimulation using a given processing scheme will generally consume more power.

A cochlear implant device such as that illustrated in FIG. 1 may be powered by zinc-air cells. Conventionally, zinc-air cells are used to power speech processor units, especially behind the ear type processors. The technology of these cells is such that even though the cell capacity is very high, only a limited current is available.

In existing devices, a battery monitor arrangement is provided in the speech processor 1. The monitor measures the output voltage from the battery, and if the voltage falls below a certain level, the monitor sends a signal to the processor which shuts down the processor. Thus a combination of adverse factors can cause the cell voltage to drop, causing the low voltage trip to operate, switching the processor off. This may happen even if the cells are new, causing unnecessary inconvenience to the patient.

According to the present invention, this problem can be overcome by reducing the power requirements of the system when the voltage drops a certain level. One way to reduce power requirements is to lower the stimulation rate being applied by the implant. Effectively power consumption is proportional to rate (apart from a small quiescent current). Although stimulation rate can have an effect on patient speech recognition performance, it is likely that the circumstances leading to such a rate reduction are situations of severe background noise such as a noisy train. When the adverse situation has passed, the rate returns to the normal programmed rate.

According to one implementation of the present invention, the stimulation rate is modulated at a rate determined by the cell voltage. When the cell voltage is above a predetermined threshold level the stimulation rate is at a pre-set normal value. When the cell voltage falls below a second predetermined threshold level, the low-voltage alarm is triggered and the speech processor shuts down in the same fashion as a prior art speech processor.

The cell voltage may be determined by various mechanisms. An analog or digital voltmeter device could be used, a software function within the processor, or simply an analog circuit arrangement responsive to certain voltage levels. Any suitable means may be used, as would be understood by those skilled in the art.

The two thresholds create an intermediate range of cell voltages within which the cell or cells are still capable of supporting some functionality, but not the full operational mode. Within this range the speech processor enters a reduced functionality mode. In one embodiment this would involve the speech processor switching to a low-power mode. It is preferable, however, that the speech processor operate at a stimulation rate which is determined by the measured cell voltage, as shown in FIG. 2.

Figure 2:
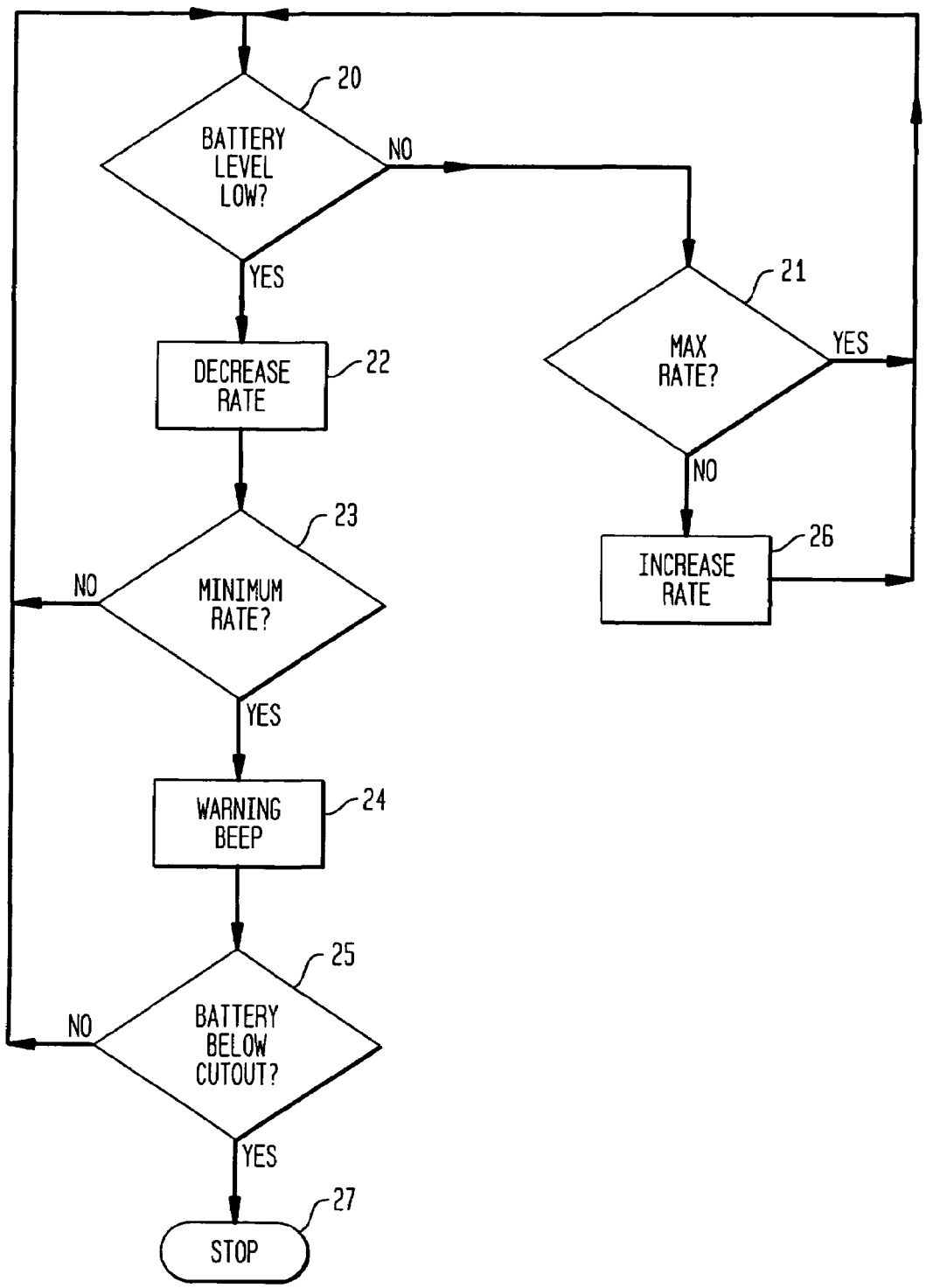
FIG. 2 is a flow chart illustrating the operation of the inventive system.

Referring to FIG. 2, a flowchart illustrating one implementation of the invention is shown. At box 20, the process determines if the battery voltage level is low, that is, below a first predetermined value. If it is, then the stimulation rate is decreased at box 22. If the value at box 20 is not below a first predetermined value, then box 21 determines if the processor is operating at its maximum stimulation rate. If it is, then the process loops back to box 20. If the rate is not at maximum, the rate is increased by a predetermined amount and the process again loops back to box 20.

If the stimulation rate has been decreased at box 22, box 23 determines if the stimulation rate is at the preset minimum rate—in other words, if it is at the minimum tolerable stimulation rate. If not, then the process loops back to box 20. If it is at minimum rate, box 24 instructs a warning beep to be provided to the user, so that the user is aware that the processor may be shut down shortly. Box 25 then tests if the battery level is below a second predetermined threshold level. If it is, then the processor is stopped at box 27 and the speech processor shuts down. If it is not at the cutoff level, the process loops back to box 20.

It will be appreciated that alternative responses to progressively lower levels could be readily implemented in a speech processor. One alternative would be to switch at a certain level to an alternative speech processing strategy, which requires less power, or provides better speech percepts at low stimulation rates. For example, at a first predetermined level the very low battery response may be to switch to another processing strategy, which copes better with progressive stimulation rate reduction than the normal strategy. Another option, for example in a processor which uses a selection of channels from a filter arrangement as a basis for stimulation, may be to reduce the number of channels processed by the filter and/or to reduce the number of channels selected as the basis for stimulation. Other alternative strategies could be used to reduce power requirements in different applications, as would be apparent to those skilled in the art. Combinations of these approaches could be used.

Preferably the method is implemented as a closed loop method. If the voltage drops below the higher threshold, the rate begins to slow gradually by introducing an additional wait period at the end of a count which determines the stimulation rate. If the voltage rises again, the wait is gradually reduced. As a result, the processor stimulates at a rate which keeps the cell voltage at close to the higher threshold. If the load increases or the cell output decreases, the rate lowers further until it is unable to keep the cell voltage at the high threshold. The result is that the voltage continues to drop until the low threshold is reached. As this point the processor cuts out.

The stimulation rate could be determined by a measure of cell voltage which incorporates some time information. This could be, for example, the average cell voltage over the last 5 minutes.

Figure 3:
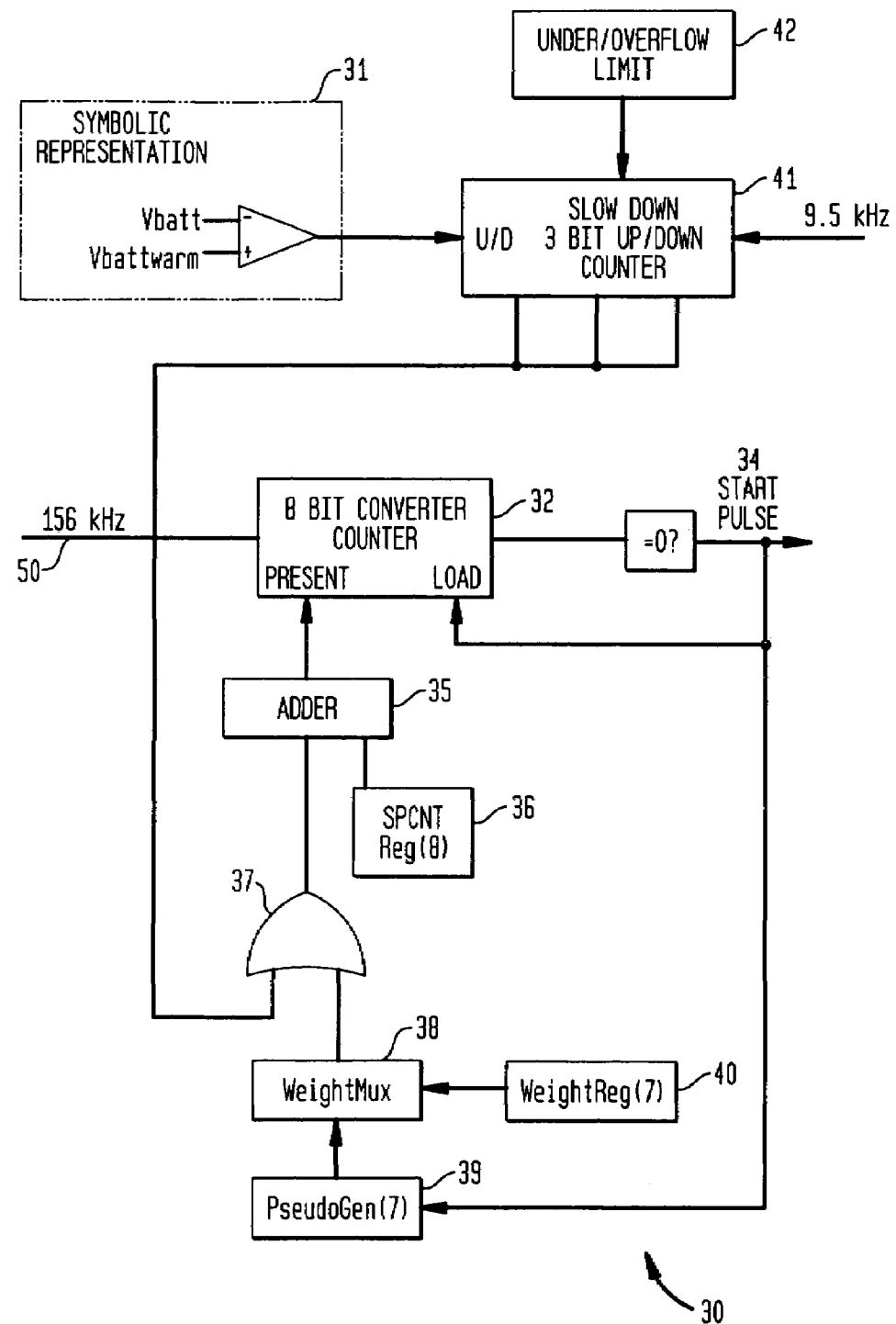
FIG. 3 is a schematic diagram of a central circuit utilising the present invention.

FIG. 3 illustrates a practical implementation of the present invention for a cochlear implant. The illustrated system is a start pulse generator 30, which generates pulses for commencing each cycle of stimulation generation by the speech processor. The pulse rate is set by a counter 32 which counts 6.4 μs ticks received on line 41. The count is set by register SPCNT 36. At count 0 the counter 32 is automatically reloaded by the output of adder 35. Input to adder 35 is the SPCNT word from register 36, and the output from a 7 bit pseudo random generator 39 with bits masked by WeightMux 38 as indicated by the weight register 40.

In order to provide the features of the present invention, the low battery warning operation is altered so that when the threshold is encountered the start pulse counter is increased. The wait is increased by modifying the top 3 bits of the 7 bit WEIGHT register 40 with a count from a 3 bit SLOWDOWN counter 41. The output of this result 37 is added to SPCNT 36 to provide the input to counter 32.

The SLOWDOWN counter 41 operates on the detection of the Batwarn signal from box 31. This is when the battery voltage drops below a first predetermined level, the Batwarn setting. When the battery voltage has dropped below this level, the SLOWDOWN counter is clocked up at the rate of 9.5 Hz. If the battery voltage is above the Batwarn level, the counter is clocked down at 9.5 Hz. At each end of its range, the counter is prevented from overflowing by box 42. By this means, the period of START PULSE (SP) is increased slowly by 16*6.4=102.4 μs steps from a minimum of 0 to a maximum of 7*102.4=716.8 μs in addition to the value set. Assuming that the SP rate is typically set to 1500 Hz, i.e. with a period of 667 μs, this means that as the battery voltage sinks below the Batwarn level, the pulse rate is gradually slowed down to approximately half of its normal rate. If the power demands lessen, the rate will increase again to the normal rate of the start pulse counter.

Jitter in the start pulses can be used in the lower 4 or 5 bits. If 5 bits of jitter are used, the period will be for example 567-767 μs for no slow down, then a bit D4 is over-ridden by the SLOWDOWN counter, the jitter will be 667-767 μs. When bit D5 is set by the counter, the jitter will be 767-967 μs etc. If 4 bits of jitter are used, the sequence will be 667, 769, 871 μs+/−51 μs. In this way the range of jitter is reduced under some circumstances but there is a gradual progression in the overall rate change.

To give the patient a warning of low battery, a beep is generated when the SLOWDOWN counter first reaches its maximum count It will be understood that the above example is merely one embodiment of the present invention, and that variations and additions are possible within the broad scope of the inventive concept, as will be apparent to those skilled in the art.

The invention claimed is:

1. A speech processor for a cochlear implant, comprising:
a battery monitor configured to measure the voltage across the output of a power source connected to the speech processor; and
a control circuit configured to downgrade performance of the speech processor when the measured voltage is below a predetermined threshold level.

2. The processor of claim 1, wherein said controller is further configured to shut down the speech processor when the measured voltage is below a second predetermined threshold level.

3. The processor of claim 1, wherein the power source comprises one or more zinc air batteries.

4. The processor of claim 1, further comprising:
a housing, wherein the power source is integrated in said housing.

5. The processor of claim 1, wherein said controller is further configured to generate an alert when said controller downgrades the speech processor performance.

6. The processor of claim 1, wherein the cochlear implant is configured to deliver stimulation pulses to a patient, and wherein said controller downgrades the performance of the speech processor by reducing the rate at which stimulation pulses are delivered to the patient.

7. The processor of claim 1, wherein the speech processor implements a first speech processing strategy when the measured voltage output is above a predetermined threshold level, and wherein said controller downgrades the performance of the speech processor by selecting an alternative speech processing strategy.

8. The processor of claim 6, wherein the rate at which stimulation pulses are delivered to the patient is based on the voltage measured across the output of the power source.

9. A method for altering power consumption of a cochlear implant having a speech processor, comprising:
measuring the voltage across the output of a power source connected to the speech processor;
comparing the measured voltage to a predetermined threshold level; and
downgrading speech processor performance when the measured voltage is below the predetermined threshold level.

10. The method of claim 9, further comprising:
comparing the measured voltage output to a second predetermined threshold level; and
shutting down the speech processor when the measured voltage is below the second predetermined threshold level.

11. The method of claim 9, further comprising:
generating an alert when said control circuit downgrades the performance of the speech processor.

12. The method of claim 9, wherein the cochlear implant is configured to deliver stimulation pulses to a recipient, and wherein downgrading the performance of the speech processor comprises:
reducing the rate at which stimulation pulses are delivered to the patient.

13. The method of claim 12, further comprising:
reducing the rate at which stimulation pulses are delivered to the patient based on the voltage measured across the output of the power source.

14. The method of claim 9, wherein the speech processor implements a first speech processing strategy when the measured voltage output is above the predetermined threshold level, and wherein downgrading the performance of the speech processor comprises:
selecting an alternative speech processing strategy.

15. A speech processor for a cochlear implant configured implement a speech processing strategy, the processor comprising:
a battery monitor configured to measure the voltage across the output of a power source connected to the speech processor; and
a control circuit configured to select one of a plurality of speech processing strategies when the measured voltage is above a predetermined threshold level, and configured to select a second speech processing strategy when the measured voltage output is below the predetermined threshold.

16. The processor of claim 15, wherein said controller is further configured to shut down the speech processor when the measured voltage output is below a second predetermined threshold level.

17. The processor of claim 15, wherein the power source comprises one or more zinc air batteries.

18. The processor of claim 15, further comprising:
a memory; and
a housing, wherein the power source and said memory is integrated into said housing.

19. The processor of claim 15, wherein said controller is further configured to generate an alert when said controller selects the second speech processing strategy.

20. The processor of claim 15, wherein at least one of the plurality of speech processing strategies results in delivery of stimulation pulses to a patient of the cochlear implant at a high rate.

21. The processor of claim 15, wherein of said second speech processing strategy results in delivery of stimulation pulses to a patient of the cochlear implant at a high rate.

22. The processor of claim 15, wherein said second speech processing strategy consumes less power from the power source than at least another one of the plurality of strategies.

23. A method for altering power consumption of a cochlear implant, comprising:
measuring the voltage across the output of a power source connected to the signal processor;
comparing the measured voltage to a predetermined threshold level; and
selecting one of a plurality of speech processing strategies when the measured voltage is above a predetermined threshold level, and selecting a second one of said plurality of strategies when the measured voltage is below the predetermined threshold.

24. The method of claim 23, further comprising:
shutting down the speech processor when the measured voltage is below a second predetermined threshold level.

25. The method of claim 23, further comprising:
generating an alert when said at least second one of said plurality of strategies is selected.

26. A speech processor for a cochlear implant configured to deliver stimulation pulses to a patient, comprising:
a battery monitor configured to measure the voltage across the output of a power source connected to the speech processor; and
a control circuit configured to reduce the rate at which stimulation pulses are delivered to the patient when the measured voltage is below the predetermined threshold.

27. The speech processor of claim 26, wherein said controller is further configured to generate an alert when said controller reduces the rate at which stimulation pulses are delivered to the patient.

28. The speech processor of claim 26, wherein said controller is further configured to shut down the speech processor when the measured voltage is below a second predetermined threshold level.

29. The speech processor of claim 26, wherein said power source comprises one or more zinc air batteries.

30. The speech processor of claim 26, further comprising:
a memory; and
a housing, wherein the power source and the memory are integrated into said housing.

* * * * *